(12) United States Patent
Beese et al.

(10) Patent No.: US 9,261,451 B2
(45) Date of Patent: Feb. 16, 2016

(54) DEVICE AND METHOD FOR DETERMINING THE PERMEATION RATE OF BARRIER ELEMENTS AND ULTRA-BARRIER ELEMENTS

(71) Applicant: Fraunhofer-Gesellschaft zur Foerderung der angewandten Forschung e.V., Munich (DE)

(72) Inventors: Harald Beese, Freital (DE); Wulf Graehlert, Dresden (DE); Stefan Kaskel, Dresden (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 410 days.

(21) Appl. No.: 13/903,110

(22) Filed: May 28, 2013

(65) Prior Publication Data
US 2013/0312491 A1 Nov. 28, 2013

(30) Foreign Application Priority Data

May 25, 2012 (DE) .......................... 10 2012 010 269

(51) Int. Cl.
*G01N 15/08* (2006.01)
(52) U.S. Cl.
CPC ........ *G01N 15/0826* (2013.01); *G01N 15/0806* (2013.01)
(58) Field of Classification Search
CPC .................................................. G01N 15/0826
See application file for complete search history.

(56) References Cited

U.S. PATENT DOCUMENTS

| 5,390,539 | A | 2/1995 | Mayer | |
|---|---|---|---|---|
| 2005/0092068 | A1* | 5/2005 | Ascheman | G01N 15/0826 73/38 |
| 2009/0320564 | A1* | 12/2009 | Piombini | G01N 15/0826 73/38 |

FOREIGN PATENT DOCUMENTS

WO WO 2008145115 A2 12/2008

OTHER PUBLICATIONS

Bernd Schirmer et al.; Experimental investigation of the water vapour concentration near phase boundaries with evaporation, Meas. Sci. Technol. 15 (2004) 1671-1682.

\* cited by examiner

*Primary Examiner* — Laura Martin
*Assistant Examiner* — Alex Devito
(74) *Attorney, Agent, or Firm* — Jacobson Holman, PLLC.

(57) ABSTRACT

The invention relates to a method and a device for determining the permeation rate of barrier elements and ultra-barrier elements according to an isostatic permeation measurement method. In the process, the convective mass transfer of a permeate permeated through a barrier element is replaced by a diffusion-controlled mass transfer along a diffusion path in a subsequently arranged measurement chamber with a hollow conducting element and permeate sink.
The permeate sink ensures that permeate is removed continuously, and so a mass flux equilibrium of the permeate is set through the barrier element and through the diffusion path.
The concentration gradient of the permeate and, from this, the permeation rate of the barrier element is then determined by non-invasive determination of the concentration of the permeate along the diffusion path.

14 Claims, 5 Drawing Sheets

DEVICE AND METHOD FOR DETERMINING THE PERMEATION RATE OF BARRIER ELEMENTS AND ULTRA-BARRIER ELEMENTS

The invention relates to a device and a method for determining the permeation rate of barrier elements and ultra-barrier elements according to an isostatic permeation measurement method.

Being able to establish the permeability of materials for particular permeates is of great importance in very different applications. Determining the permeation rate is desirable, particularly in the development phase of polymer materials and barrier layers formed thereon, for layer systems and also for quality control in the production process. This relates to permeation barrier-forming elements, in particular films, membranes, plates, tubular and annular elements, or components which can also be made of or with composite materials. By way of example, the permeation rate of such materials, which are used for encapsulation, determines to great extent the function and the quality of OLED displays, LCD displays, thin-layer solar cells, organic solar cells and other electronic components, and also the shelf-life of foodstuffs and pharmaceutical products. Satisfying the demand for materials with the lowest possible permeation rates, in particular for $O_2$ and $H_2O$, by the use of novel materials with ultra-barrier properties simultaneously requires the assured quantitative detection of very small permeation rates.

The methods for determining the permeation rate of ultra-barrier materials require a very sensitive measurement system due to very low permeate concentrations. Conventional measurement methods, such as, for example, the gas detection, known from U.S. Pat. No. 5,390,539, with non-dispersive infrared sensors or methods with coulometric moisture sensors do not achieve the desired measurement sensitivity in order to be able to determine very low permeation rates in the region of $<10^{-4}$ g $[H_2O]$ $m^{-2}$ $d^{-1}$.

To date, isostatic measurement methods are known, in which the permeation rate of barrier materials is established using a permeate-containing carrier gas. Here, a constant permeate mass flux or an equilibrium permeate concentration is set. The constant permeate mass flux then is a measure for the gas permeability or the permeation rate of the barrier material. However, even in the case of laser-based detection systems and very small carrier gas flows of 3 sccm, the detection limit lies at the detection limit. However, a further reduction in the carrier gas flow means that, if very low permeate concentrations are present, an even longer settling time until the equilibrium state is reached is moreover required and, furthermore, this leads to significantly larger degrees of uncertainty when determining the permeate mass flux, which in turn is expressed directly in the error when determining the permeation rate.

WO 2008/145115 A2 has disclosed a device and a method for measuring the permeation of an element which forms a permeation barrier, wherein, in the case of a permeate which permeated through a barrier-forming element, an attenuation of the intensity of a laser beam, measurable at a detector is brought about, and the permeation rate is determined depending on the time. Here, the laser beam is guided through a detection chamber, through which a gas continuously flows, in order to remove the permeated permeate. However, the problem here, once again, is that very low permeation rates, such as of ultra-barrier materials, for example, cannot be detected or can only be detected insufficiently on account of the low measurement sensitivity.

Furthermore, the work by Bernd Schirmer, entitled "Hochaufgelöste Wasserdampfdetektion mittels Diodenlaser-Absorptionsspektroskopie" [High-resolution water vapour detection by means of diode-laser absorption spectroscopy] (2001, Stuttgart, Erlangen-Nurnberg), has disclosed a detection system in which the permeation rate can be determined on the basis of a water vapour concentration gradient. However, this method is only suitable for measuring very high permeation rates.

It is therefore an object of the invention to provide a device and a method with sufficient sensitivity for determining the permeation rate of barrier elements.

The solution of the object, according to the invention, takes into account the fact that the convective mass transfer of a gas to be permeated from a test gas space, which can also be referred to as examination gas space, feed side or vapour space, through a barrier element into a subsequently arranged measurement chamber with hollow conducting element and permeate sink is replaced by a diffusion-controlled mass transfer. This means that a permeate (matter which is permeated from the test gas space through a barrier element) diffuses without flow in an inert gas atmosphere along a diffusion path of known length, up to a permeate sink, and is absorbed or otherwise removed from there. Here, the permeate sink ensures a constant and low concentration of the permeate. As a result of the permeate sink, a concentration gradient is formed over the diffusion path. Here, the concentration gradient constitutes the driving force and cause of the diffusion.

According to Fick's first law (1), $$J = -D * \Delta c / \Delta x, \quad (1)$$

the concentration gradient ($\Delta c/\Delta x$) of the permeate counter to the diffusion direction is proportional to the particle flux density J (flow speed of the permeate through the diffusion path). Here, the constant of proportionality D is the diffusion coefficient of the permeate.

In the case of constant permeation of the gas, to be permeated, through the barrier element, the permeate mass flux $M_B$ through the barrier element equals the permeate mass flux $M_G$ through the gas atmosphere in the diffusion path. In this case, a constant concentration profile is set.

In general, the mass flux M describes a mass which passes through a cross-sectional area A in a unit time.

For a solid body, such as, for example, in the case of a barrier element, the permeate mass flux $M_B$ then, in accordance with Equation (2), emerges from the product of the permeation rate $PR_B$ of the solid body and the permeable area $A_B$ of the solid body.

$$M_B = PR_B * A_B \quad (2)$$

When considering the gas atmosphere of the diffusion path, through which the permeate can diffuse, adjoining thereafter, the permeate mass flux $M_G$ emerges in accordance with Equation (3) from the particle flux density J (particles which diffuse through a cross-sectional area perpendicular to the diffusion flux per unit time) and the respective associated cross-sectional area $A_G$, through which diffusion can occur, of the diffusion path:

$$M_G = J * A_G. \quad (3)$$

In the case of a constant permeate mass flux M in the whole system ($M_B = M_G$), the following applies:

$$PR_B * A_B = J * A_G, \quad (4)$$

$$PR_B * A_B = -D * \Delta c / \Delta x * A_G, \quad (5)$$

$$PR_B = -D * \Delta c/\Delta x * A_G/A_B, \quad (6)$$

and so the permeation rate $PR_B$ of the solid body (barrier element) can be calculated using Equation (6) using knowledge of the concentration gradient $\Delta c/\Delta x$ forming in the gas atmosphere of the diffusion path. What applies in this case is that the change in the concentration of the permeate over the barrier element is greater than the change in the permeate concentration over the diffusion path by at least a factor of 100 so that the permeation through the barrier element is not influenced by the measurement.

In order to measure the permeate concentration, use is made of a measurement method in which the measurement takes place in a non-invasive manner. Here, the permeate concentration is measured in such a way that permeate is not used up and the permeate concentration is not influenced. It is for this reason that an optical sensor/detector should be used.

A corresponding device according to the invention for determining the permeation rate of a barrier element or an ultra-barrier element has a measurement chamber, which is separated from a test gas space by a barrier element. Gas to be permeated is contained in the test gas space and/or said gas is continuously supplied and removed. Here, a constant partial pressure of the respective gas to be permeated is maintained at all times.

The barrier element forms a separation with a known permeable cross-sectional area $A_B$ with respect to the measurement chamber, at least in sections. At least one hollow conducting element with a permeate sink is arranged or formed on such a measurement chamber in such a way that a flow-free diffusion path, through which a permeate can diffuse, is formed starting from the barrier element, through the hollow conducting element, up to the permeate sink. The hollow conducting element can be formed by a channel-like or pipe-like element and can have a heating apparatus. The end of a hollow conducting element opens into a permeate sink. Permeate can be continuously removed by adsorbers and/or absorbers at the permeate sink. By way of example, if use is made of water vapour permeates, zeolites can be used to remove the water vapour. Furthermore, use can be made of a permeate sink which, for example, is embodied as a T-piece with a large cross section and continuously purged using a dry gas containing no permeate.

At least the measurement chamber and the hollow conducting element are sealed with respect to the surrounding atmosphere in a pressure-tight and fluid-tight manner such that it is ensured that, in order to form an equilibrium mass flux or in order to form a constant concentration gradient of the permeate, a flow-free gas atmosphere is set within the diffusion path and permeate reaches the permeate sink only as a result of diffusion through the diffusion path. In particular, there should not be any leakage points at the connection points of individual elements which lead to the ingress of moisture because the formation of the concentration gradient could otherwise be superposed in an interfering fashion.

The clear internal cross-sectional area $A_G$ of a hollow conducting element should be less than or greater than the cross-sectional area $A_B$ at at least one position. Here, a reduced clear internal cross-sectional area $A_G$ is preferred.

A concentration gradient of the permeate forms along the diffusion path, starting from the barrier element in the direction of the permeate sink, for the aforementioned case of a constant permeate mass flux in the whole system ($M_B = M_G$).

At at least one position along the diffusion path, a hollow conducting element has a clear internal cross-sectional area $A_G$ which is modified compared to the permeable cross-sectional area $A_B$ of the barrier element. The change in internal cross section along the diffusion path can in this case be jump-like and/or continuous, for example as a result of conical shaping or tapering in sections.

Furthermore, a hollow conducting element can be formed of stainless steel and have surface-treated internal walls, such as an electropolished surface, for example. The internal clear cross-sectional area $A_G$ of a hollow conducting element can also have various internal cross-sectional profiles (round, polygonal or irregular) with a known area $A_G$.

In an advantageous embodiment of a hollow conducting element, the clear cross-sectional area $A_G$ along the diffusion path can be modified by varying the opening of a stop, such as, for example, in the case of a diaphragm. At least one such stop can be arranged within a hollow conducting element at at least one position along the diffusion path. Here, such a stop can be formed in such a way that the diffusion path can be sealed in a pressure-tight and fluid-tight manner.

In order to reduce the risk of leakage rates, all connection points of the measurement chamber, the hollow conducting elements and the test gas space should be joined in a pressure-tight and fluid-tight manner, for example by soldering or welding.

Furthermore, a hollow conducting element can have a meandering profile structure such that it is possible to achieve a lengthening of the diffusion path. Here, the length of the diffusion path can be greater than the distance between the measurement chamber and the permeate sink. As a result of this, it is possible to realize a more compact design and good accessibility to the measurement of the permeate concentration.

A purging gas, which should have a flow speed that is kept constant, can flow within the permeate sink. Here, the flow speed must be set in such a way that neither negative pressure ("water beam pump effect") nor turbulence can be created in the measurement chamber and the hollow conducting element. In order to reduce interference of the concentration gradient, a membrane permeable to the permeate, such as e.g. a porous material or a filter, can be arranged at the opening of the hollow conducting element (at the connection point to the permeate sink).

Radiation from at least one radiation source, the radiation having at least one wavelength corresponding to an absorption wavelength of the respective permeate, but at least lying in a tightly delimited wavelength range around such an absorption wavelength of a permeate, can be emitted through window elements in a hollow conducting element and/or through a hollow conducting element which is optically transparent, at least in regions.

The radiation must be guided through a volume element d of the diffusion path with a known length, at a position $x_i$ along the diffusion path, with a known distance from the barrier element or from the permeate sink, and directed at at least one optical detector, which is suitable for determining an intensity of at least one respective absorption wavelength of the permeate. Here, the distance of the position $x_i$ from the barrier element or from the permeate sink corresponds to the absolute path length of the diffusion path. The radiation can be guided perpendicular to or along through a volume element d of the diffusion path.

In an advantageous embodiment of a hollow conducting element, optical elements, such as prisms, lenses or fibres, can be used for beam guidance of the radiation within the hollow conducting element. Furthermore, the radiation source and the detector can be arranged within a hollow conducting element, wherein the internal wall of a hollow conducting element can be employed as a reflecting element.

By way of example, the positioning and the guidance of the radiation along the diffusion path can be modified by displacing the radiation source and the detector on a linear unit or by fibre-coupled optical units and an optical multiplexer.

In a further embodiment of the device, the measurement chamber, together with a hollow conducting element and a permeate sink, can be interchanged by a type of changer system or manually inserted into the device from a climate chamber, for example after a conditioning time. To this end, the measurement chamber and/or the hollow conducting element can be provided with valves for pressure-tight and fluid-tight sealing with respect to the atmosphere of the surroundings. A measurement chamber in conjunction with the hollow conducting element and the permeate sink can therefore be embodied as an autonomous unit such that the device can be equipped with a plurality of samples to be measured (a plurality of measurement chambers with hollow conducting element and permeate sink). Here, the measurement of a plurality of samples using a radiation source and a detector can occur simultaneously.

In a special embodiment of the device, at least two hollow conducting elements with mutually different clear internal cross-sectional areas $A_G$ are arranged in parallel between the measurement chamber and the permeate sink. Here, the internal clear cross-sectional areas $A_G$ of the hollow conducting elements can differ from the cross-sectional area $A_G$. Moreover, the respective hollow conducting elements can have valves or stops which serve for pressure-tight and fluid-tight sealing of the diffusion path.

In a further advantageous embodiment, a second barrier element with a known permeability/permeation rate is arranged following a first measurement chamber and a second measurement chamber is arranged following the second barrier element. In this embodiment, the second arrangement of barrier and measurement chamber is used as replacement for the diffusion path of the first measurement chamber. The known permeation/diffusion resistance of the second barrier element can therefore be used for determining the permeation rate of the first barrier element. By way of example, the water vapour permeability $WDD_2$ of the unknown barrier element can be calculated by virtue of initially establishing the mass flux $m'_1$ through the known barrier element. This is calculated by:

$$m'_1 = WDD_1 * \Delta c_1 * A_1 / d_1, \quad (7)$$

where $WDD_1$ is the water vapour permeability of the known barrier element, $\Delta c_1$ is a change in concentration over the known barrier element, $A_1$ is of the known barrier element and $d_1$ is the thickness of the known barrier element.

Under the assumption that $\Delta c_1$ (change in concentration over the known barrier element) $<<\Delta c_2$ (change in concentration over the unknown barrier element to be measured), the water vapour permeability $WDD_2$ through the unknown barrier element can be determined in a simplified fashion by the following equation:

$$WDD_2 = m'_1 * A_2 \text{ (if } m'_1 = m'_2 \text{ applies).} \quad (8)$$

Alternatively, it is possible to carry out a correction calculation to remove the smaller concentration gradient, caused by the measurement, over the unknown sample to be measured by means of the following equation:

$$WDD_2 = WDD_1 * \Delta c_{1,2} / \Delta c_{1,2} - \Delta c_1, \quad (9)$$

where $WDD_2$ is the water vapour permeability of the unknown barrier element to be measured, $WDD_1$ is the water vapour permeability of the known barrier element, $\Delta c_{1,2}$ is the change in concentration over both barrier elements and $\Delta c_1$ is the change in concentration over the known barrier element.

In the case of a method according to the invention for determining the permeation rate of a barrier element, at least one gas to be permeated is continuously supplied to and/or kept at constant partial pressure in the test gas space.

All condensable, non-condensable, toxic and combustible gaseous substances and vapours and/or vapour mixtures come into question as permeates. By way of example, this applies to CO, $CO_2$, $NH_3$, $SF_6$, petrol vapours, benzene, aromas, solvent vapours (acetone, 2-propanol) and isotopes thereof. However, water vapour should preferably be used as permeate for determining the permeation rate of a barrier element.

The permeate permeated through a cross-sectional area $A_B$ of a barrier element reaches a measurement chamber and, from there, diffuses along a diffusion path through at least one hollow conducting element with at least one clear cross-sectional area $A_G$, which is different from the cross-sectional area $A_B$, to a permeate sink and there it is adsorbed and/or absorbed and/or removed by a dry purge gas such that a constant permeate concentration below the detection limit is set at the permeate sink. Here, the concentration of the permeate at the permeate sink can equal zero.

At the same time, radiation having at least one absorption wavelength of a respective permeate, which is emitted by at least one radiation source is directed through the measurement chamber and/or through at least one hollow conducting element, guided through one volume element d of the diffusion path at at least one known position $x_i$ in the case of a single-position measurement and through respectively one volume element $d_i$, $d_{ii}$ of the diffusion path at at least two known positions $x_i$, $x_{ii}$ in the case of a multiple position measurement, and directed at at least one optical detector, and, in the process, the intensity modification of the radiation as a result of the permeate concentration is detected and the permeate concentration c is determined therefrom.

In the case of the single-position measurement, the known position $x_i$ along the diffusion path corresponds to the absolute path length of the diffusion path between the position $x_i$ and the barrier element or the permeate sink.

The concentration $c_i$ of the permeate at the position $x_i$, or, in the case of a multiple position measurement, the permeate concentrations $c_i$ and $c_{ii}$ at the positions $x_i$ and $x_{ii}$, is/are then determined on the basis of the Beer-Lambert law:

$$-lg(I_1/T_0) = \epsilon * c * d. \quad (10)$$

As described at the outset, a concentration gradient of the permeate forms along the diffusion path in the equilibrium state ($M_B = M_G$). By determining the permeate concentration at two different positions $x_i$ and $x_{ii}$ along the diffusion path, it is possible to determine the change in the permeate concentration $\Delta c$ (two-position measurement). Here, the absolute path length of the diffusion path between the two positions $x_i$ and $x_{ii}$ corresponds to a diffusion path section $\Delta x$. Knowing $\Delta c$ and $\Delta x$ then renders it possible to determine the concentration gradient of the permeate. In the case where the diffusion constant D of a respective permeate is not known from reference works, it can be determined using reference barrier elements with known permeation rates. The diffusion constant D can also be carried out by an isostatic measurement according to a carrier gas method in the case of a relatively large concentration gradient or relatively large area (of the barrier element).

The permeation rate $PR_B$ of the barrier element is then calculated using the aforementioned Equation (6) from the concentration gradient of the permeate $\Delta c/\Delta x$, formed by $\Delta c$ and the length of the diffusion path section Δx, multiplied by the quotient from the clear cross-sectional area $A_G$ of the diffusion section Δx and the permeable cross-sectional area $A_B$ of the barrier element ($A_G/A_B$), multiplied by the negative value of the diffusion constant D of the permeate.

In the case of the single-position measurement, radiation is only guided along or perpendicular through a volume element d of the diffusion path through the diffusion path at one known position $x_i$. Under the assumption that the permeate concentration at the permeate sink is continuously equal to zero, the permeate concentration $c_i$ determined at the position $x_i$ corresponds to the change in permeate concentration Δc. Accordingly, the absolute path length of the diffusion path between the position $x_i$ and the permeate sink corresponds to the diffusion path section Δx.

Instrument-dependent measurement errors (radiation source, secondary electronics), which would increase the measurement error in the case of an independent measurement (at different locations), can be minimized by a comparative measurement (comparative use of the same beam source). To this end, the radiation from a beam source can, for example, be split by a beam splitter and then be simultaneously guided through the diffusion path at two positions, directed at two detectors.

For the purposes of an optimum measurement, the target region of the permeation rate should be known. Hence, it is possible to select in advance an appropriate measurement chamber with hollow conducting element and permeate sink, with adapted parameters $A_G$ and Δx. The permeate concentration in the measurement chamber and in the hollow conducting element can moreover be set by modifying the cross-sectional area $A_B$ of the barrier element to be examined. To this end, the test gas space can have a stop, by means of which the cross-sectional area $A_B$ can be varied.

In order to increase the dynamic range when setting the parameters ($A_B$, $A_G$, Δx), there can, when examining unknown samples, be a measurement, carried out in parallel (in time and space), with significantly different parameters, in which a plurality of hollow conducting elements, which can have different clear internal cross-sectional areas $A_G$ with respect to one another, can be arranged parallel to one another in the direction of the permeate sink, starting from the measurement chamber. In the case where the measured permeate concentration lies outside of the measurement range, the hollow conducting elements can then be selectively opened or sealed using valves or stops, as a result of which the diffusion path and the diffusion cross section $A_G$ and/or $A_B$ can be varied.

Laser-diode spectroscopy should preferably be used as measurement method. However, it is also possible to use a quantum cascade laser, a lead-salt laser or a fibre laser as radiation source. The connection with FTIR spectroscopy, cavity-ring-down spectroscopy, photoacoustic spectroscopy and further optical spectroscopic techniques (dispersive, non-dispersive) in different spectral ranges can likewise be advantageous. In principle, use can be made of all sensors/detectors operating on non-invasive principles, such as e.g. capacitive and spectroscopic (optical, microwave, THz) sensors, which do not use up the permeate or do not interfere with the concentration gradient of the permeate.

The permeation rate should be determined under application conditions of the barrier element in a temperature range between −20° C. and 85° C. and at atmospheric conditions. The measurement can start when the concentration gradient of the permeate is constant (mass flux in equilibrium $M_B=M_G$). The temperature should be kept constant during the measurement because adsorption and desorption processes are strongly temperature-dependent and can have an influence on the measurement. The likewise temperature-dependent diffusion constant D of the respective permeate is known or can, alternatively, be established on the basis of reference barrier elements with known permeability.

Since the diffusion along the diffusion path is very slow, the time until reaching the equilibrium state depends firstly on the length of the diffusion path and secondly on adsorption and desorption processes. In the case of hollow conducting elements with ever smaller clear internal cross-sectional areas $A_G$, there is an increase in the ratio of the number of particle collisions of the permeate with the wall atoms of the measurement element and/or the hollow conducting element compared to the number of particle collisions of the permeate with further gas atoms. This is also accompanied by an increase in the probability of an adsorption, since the desorption probability is significantly lower (the time until the permeate particle is desorbed again is significantly longer), as a result of which the diffusion along the diffusion path is slowed down. This causes very long settling times until the permeate mass flux is in equilibrium.

In order to counteract this, a hollow conducting element can be preconditioned by purging with a dry inert gas, by thermal desorption, UV irradiation or by means of a reactive gas. Since the methods for preconditioning are not suitable for samples, such as e.g. films, the measurement chamber and the hollow conducting elements can be sealed off during the sample interchange by means of valves or stops.

The formation of a concentration gradient of the permeate can be accelerated by virtue of the measurement chamber and the hollow conducting element being successively purged by a dry gas. In the process, the permeate concentration within the measurement chamber and the hollow conducting element likewise successively approaches the equilibrium state. During the purging, dry gas is, starting from the permeate sink, guided through a hollow conducting element and released via a valve which is arranged under the barrier element on the measurement chamber. By way of example, air, $O_2$, He, Ar, $H_2$ and preferably $N_2$ can be used as dry gas.

The measurement sensitivity can be influenced and set by the length of the diffusion path, the length of the diffusion path section Δx, the path length of the volume element d of the diffusion path irradiated by the radiation and/or the change in the ratio of the clear cross-sectional areas $A_B/A_G$. Accordingly, the measurement sensitivity can be increased by reducing the clear cross-sectional area $A_G$ compared to the clear cross-sectional area $A_B$. Moreover, the measurement sensitivity can be increased by lengthening the diffusion path on its own or in combination with a reduced clear cross-sectional area $A_G$ along the diffusion path. However, it is also possible to modify the ratio between the diffusion path section Δx and the clear cross-sectional area $A_G$ in order to increase the measurement sensitivity. This is the case, for example, if a hollow conducting element is formed as a capillary in sections and/or if the diffusion path section Δx is increased. Furthermore, the measurement sensitivity can be increased by lengthening the optical path length of the radiation through a volume element d of the diffusion path. However, here the precondition that the clear internal cross-sectional area $A_G$ is constant throughout along the volume element d through which the radiation is guided along the diffusion path should be satisfied. Moreover, use can also be made of combinations of the aforementioned measures for modifying the measurement sensitivity such that a measurement sensitivity is reached at which permeation rates in the range of $10^{-3}$ g [$H_2O$] $m^{-2}$ $d^{-1}$ to $10^{-6}$ g [$H_2O$] $m^{-2}$ $d^{-1}$ can be determined.

In the following text, the present invention will be described on the basis of a plurality of exemplary embodiments. Here.

Apart from the respectively explained special embodiments, the elements and parameters in FIGS. 2a to 5a correspond to the example in FIG. 1, described below, and are provided with the same reference signs.

Figure 1A:
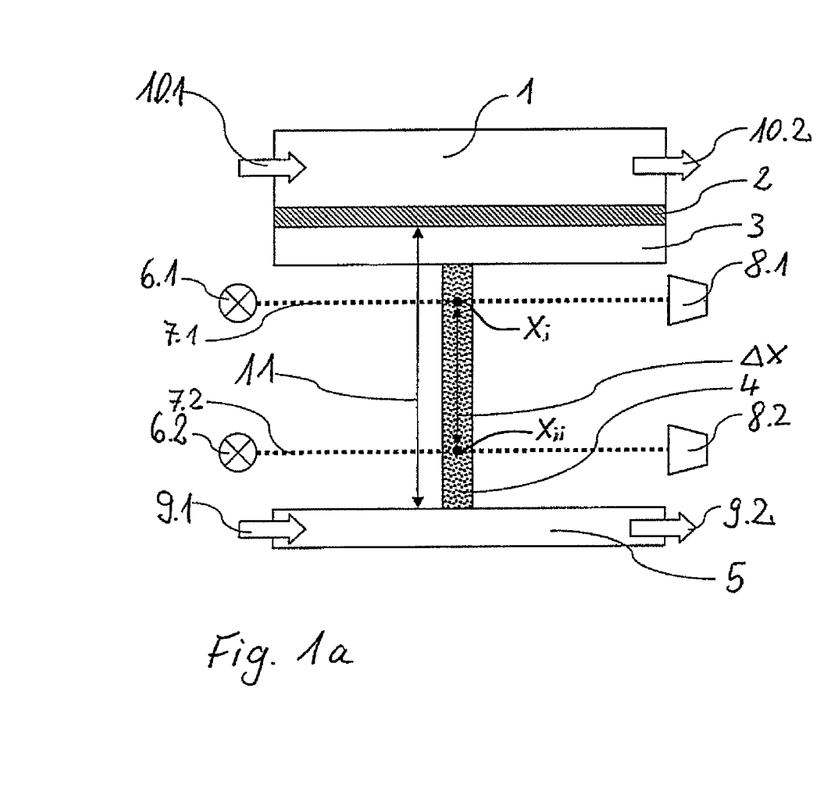
FIGS. 1a/b show a first device according to the invention with a two-position measurement perpendicular to the diffusion path, with an associated graph of the permeate concentration gradient (FIG. 1b), FIGS. 2a/b show an embodiment of a device according to the invention with a two-position measurement along the diffusion path, with an associated graph of the permeate concentration gradient (FIG. 2b), FIGS. 3a/b show an embodiment of a device according to the invention with a single-position measurement perpendicular to the diffusion path, with an associated graph of the permeate concentration gradient (FIG. 3b), FIGS. 4a/b show an advantageous one of the devices according to the invention, with hollow conducting elements arranged in parallel and the associated graph of the permeate concentration gradient (FIG. 4b), and FIGS. 5a/b show a further advantageous device according to the invention with a second barrier element and the associated graph of the permeate concentration gradient (FIG. 5b).

In the device illustrated in FIG. 1a, water vapour (gas to be permeated) is continuously supplied with 30 sccm at a constant pressure of 1013 mbar to a test gas space 1 via an inlet 10.1 and removed via an outlet 10.2. The test gas space 1 has an opening with a cross-sectional area $A_B$, which is separated from a measurement chamber 3 by a planar barrier element 2. Proceeding from the test gas space 1, water vapour can permeate through the barrier element 2 into the measurement chamber 3 via a cross-sectional area $A_B$. From there, the water vapour then diffuses along a diffusion path 11 through a hollow conducting element 4, with a cross-sectional area $A_G$, into a permeate sink 5, which is embodied as a T-piece with an internal diameter of 40 mm. A gas atmosphere with a dry gas is formed within the hollow conducting element. By way of example, air, $O_2$, He, Ar, $H_2$ and preferably $N_2$ can be used for forming the gaseous phase. Here, 30 sccm of dry purging gas, which should correspond to the gas of the gas atmosphere in the hollow conducting element 4 and be fed through a purge-gas inlet 9.1 and removed by a purge-gas outlet 9.2, continuously flows through the permeate sink 5. The water vapour is therefore removed continuously, without a "water beam pump effect" or turbulence being created within the diffusion path 11. The test gas space 1, the measurement chamber 3 with hollow conducting element 4 and the permeate sink 5 are sealed from the surrounding atmosphere in a pressure-tight and fluid-tight manner.

Figure 1B:
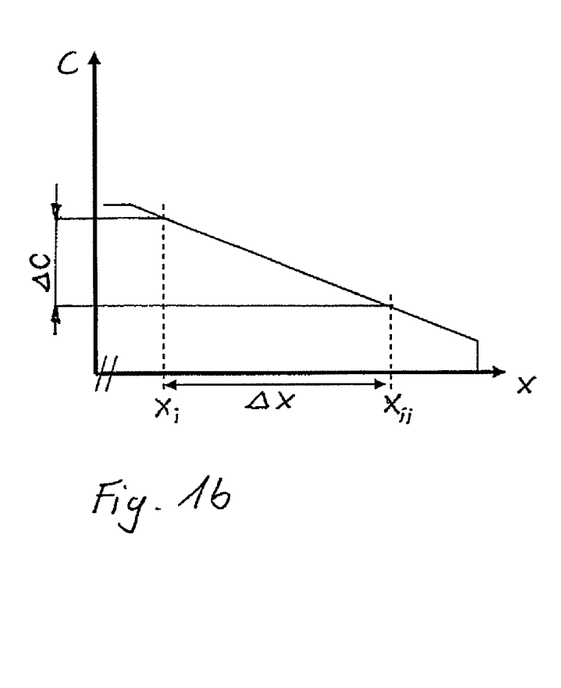

A mass flux equilibrium of the water vapour through the barrier element 2 and through the diffusion path 11 is set. Here, a water vapour concentration gradient forms along the diffusion path 11. The water vapour concentration drops off in the direction of the permeate sink 5, as illustrated in FIG. 1b. Now the water vapour concentration is determined at two different positions $x_i$ and $x_{ii}$ along the diffusion path 11 by means of laser diode spectroscopy (LDS). To this end, a first laser beam 7.1 having a wavelength corresponding to an absorption wavelength of water vapour is emitted by a laser diode 6.1 and, at a position $x_i$, guided through a window element (not shown) in the hollow conducting element 4, perpendicular through a volume element $d_i$ (not shown) of the diffusion path 11, directed at a first detector 8.1, and a second laser beam 7.2 having a wavelength corresponding to an absorption wavelength of water vapour is emitted by a laser diode 6.2 and, at a position $x_{ii}$, guided through a second window element (not shown) in the hollow conducting element 4, perpendicular through a volume element $d_{ii}$ (not shown) of the diffusion path 11, directed at a second detector 8.2. Here, the change in intensity of the laser beam 7.1 caused by the water vapour concentration at the position $x_i$ is measured at the first detector 8.1 and the change in intensity of the laser beam 7.2 caused by the water vapour concentration at the position $x_{ii}$ is measured at the second detector 8.2. The respective water vapour concentrations $c_i$ and $c_{ii}$ at the points $x_i$ and $x_{ii}$ are then calculated on the basis of the Beer-Lambert law (Equation 10). By determining $\Delta c$ (difference between $c_i$ and $c_{ii}$) and the diffusion path section $\Delta x$ (path length of the diffusion path between $x_i$ and $x_{ii}$), the concentration gradient of the water vapour is then established along the diffusion path 11. Equation (6) is then used to calculate the water vapour permeation rate through the barrier element 4.

The following Table 1 illustrates exemplary calculations for the water vapour permeation through a film.

TABLE 1

| | Trial | | | | | |
| --- | --- | --- | --- | --- | --- | --- |
| | 1 | 2 | 3 | 4 | 5 | 6 |
| D [m$^2$/s] at 25° C. | 2.60E−05 | 2.60E−05 | 2.60E−05 | 2.60E−05 | 2.60E−05 | 2.60E−05 |
| $\Delta x$ [m] | 0.5 | 0.5 | 0.5 | 1 | 10 | 0.5 |
| $A_B$ [m$^2$] | 1.35E−02 | 1.35E−02 | 1.35E−02 | 1.35E−02 | 1.35E−02 | 1.35E−02 |
| $A_G$ [m$^2$] | 1.26E−05 | 1.26E−05 | 1.26E−05 | 1.26E−05 | 1.26E−05 | 7.85E−09 |
| $\Delta c$ [g[H$_2$O]/m$^{-3}$] | 0.023873 | 0.002387 | 0.000239 | 0.000477 | 0.004775 | 0.381967 |
| $\Delta c$ [ppm] | 29.71 | 2.97 | 0.30 | 0.59 | 5.94 | 475.34 |
| PR$_B$ [g[H$_2$O]m$^{-2}$d$^{-1}$] | 1.00E−04 | 1.00E−05 | 1.00E−06 | 1.00E−06 | 1.00E−06 | 1.00E−06 |

Figure 2A:
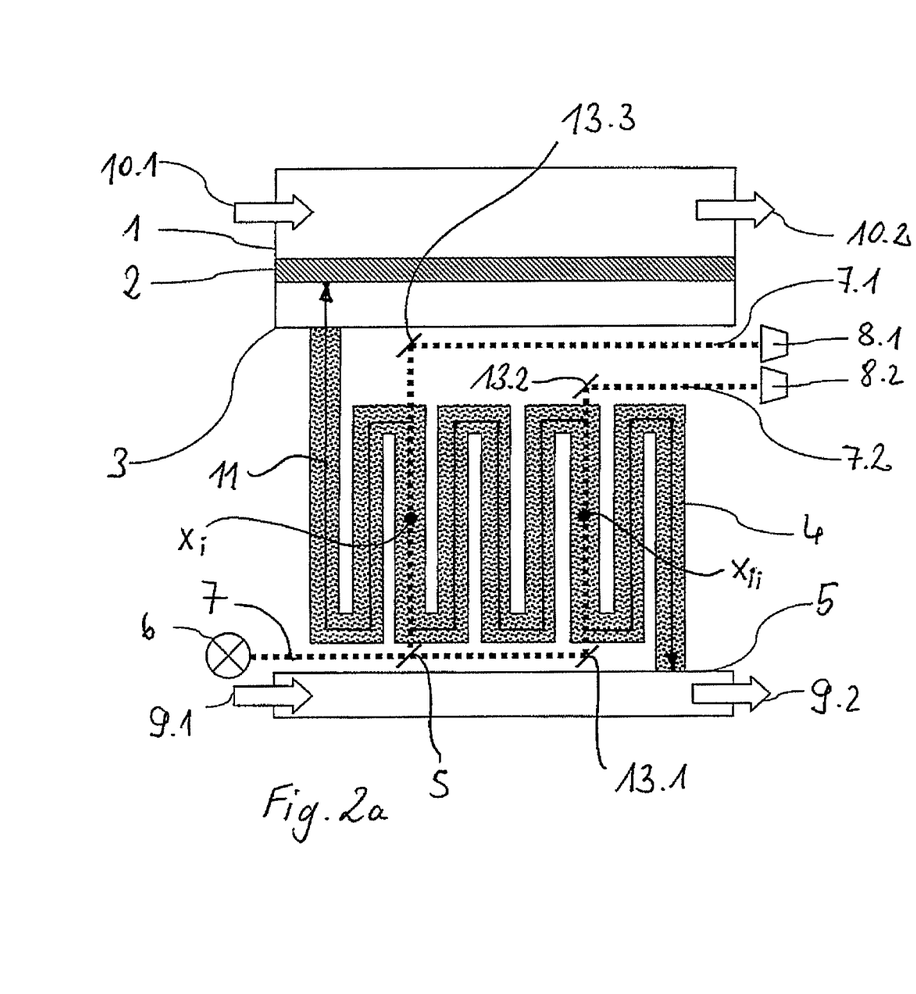
Figure 2B:
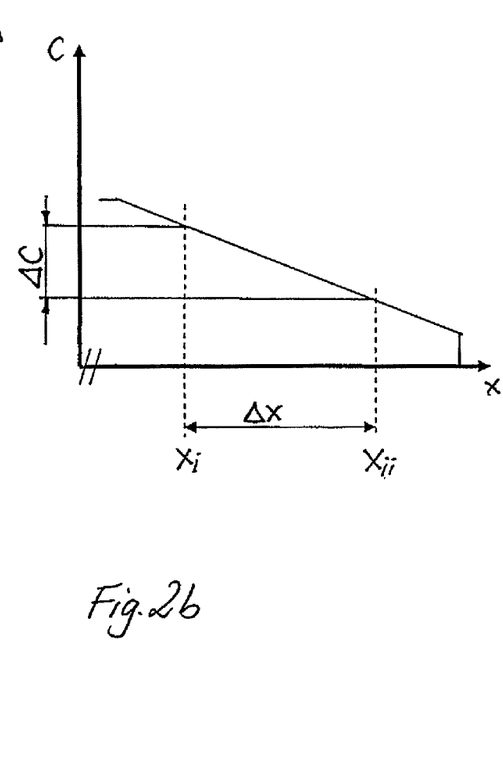

FIG. 2a shows an embodiment of the device described in FIG. 1a, in which, in order to increase the measurement sensitivity, a meandering hollow conducting element 4 with a diffusion path 11 lengthened thereby is used. Furthermore, the laser beam 7 emitted by a laser diode 6 is split into two laser beams 7.1 and 7.2 at a beam splitter S. Here, the laser beam 7.1 is guided through window elements (not shown) in the hollow conducting element 4, along through a volume element $d_i$ (not shown), with a constant cross-sectional area $A_G$, along the diffusion path 11 and directed at a detector 8.1 by means of a reflecting element 13.3. The laser beam 7.2 is guided by means of a reflecting element 13.1 through window elements (not shown) in the hollow conducting element 4, along through a volume element $d_{ii}$ (not shown), with a constant cross-sectional area $A_G$, along the diffusion path 11 and directed at a detector 8.2 by means of a reflecting element 13.2. Here, the position $x_i$ corresponds to halfway in the volume element ($d_i/2$) through which the laser beam 7.1 radiates and the position $x_{ii}$ corresponds to halfway in the volume element ($d_{ii}/2$) through which the laser beam 7.2 radiates. As a result, in this case, the diffusion path section $\Delta x$ corresponds to the path length between $d_i/2=x_i$ and $d_{ii}/2=x_{ii}$.

Figure 3A:
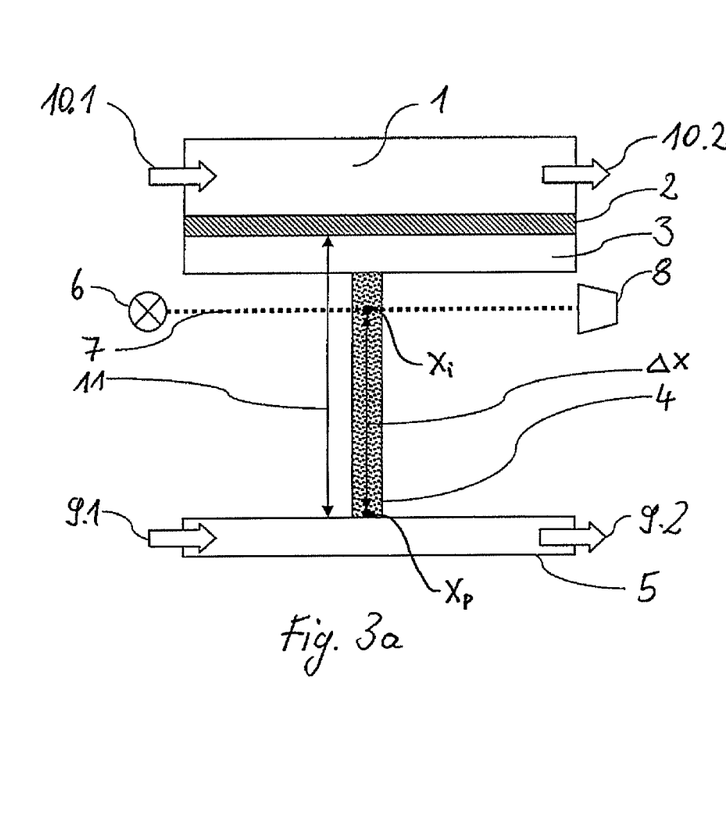
Figure 3B:
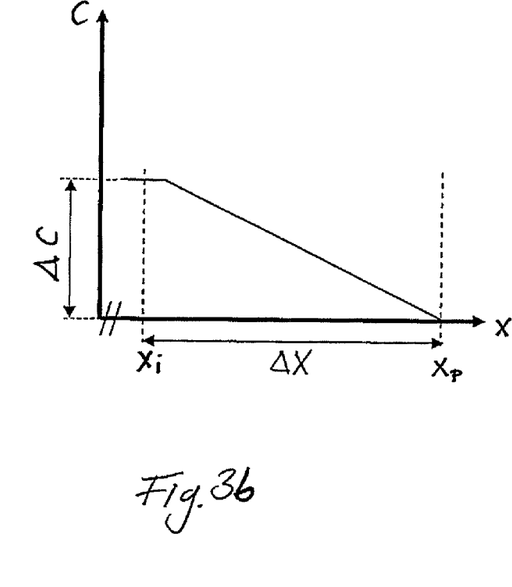

FIG. 3a shows the schematic illustration of a device as in FIG. 1a, with the difference that the concentration gradient of the permeate ($\Delta c/\Delta x$) is determined by the measurement at only one position $x_i$ along the diffusion path 11 (single-position measurement). Here, a laser beam 7 with a wavelength corresponding to an absorption wavelength of the permeate is emitted by a laser diode 6 and, at a known position $x_i$, guided through window elements (not shown) in the hollow conducting element 4, perpendicular through a volume element d (not shown) of the diffusion path 11 and directed at a detector 8.

As a result of the continuous removal of the permeate in the permeate sink 5, the concentration of the permeate at the position $x_p$ (opening of the diffusion path 11) becomes very small. Under the assumption that the permeate concentration at the position $x_p$ in the permeate sink 5 is constantly equal to zero, the change in the permeate concentration $\Delta c$ corresponds to the permeate concentration $c_i$ at the position $x_i$. The diffusion path section $\Delta x$ then corresponds to the distance between the position $x_i$ and the position $x_p$ at the permeate sink 5.

Figure 4A:
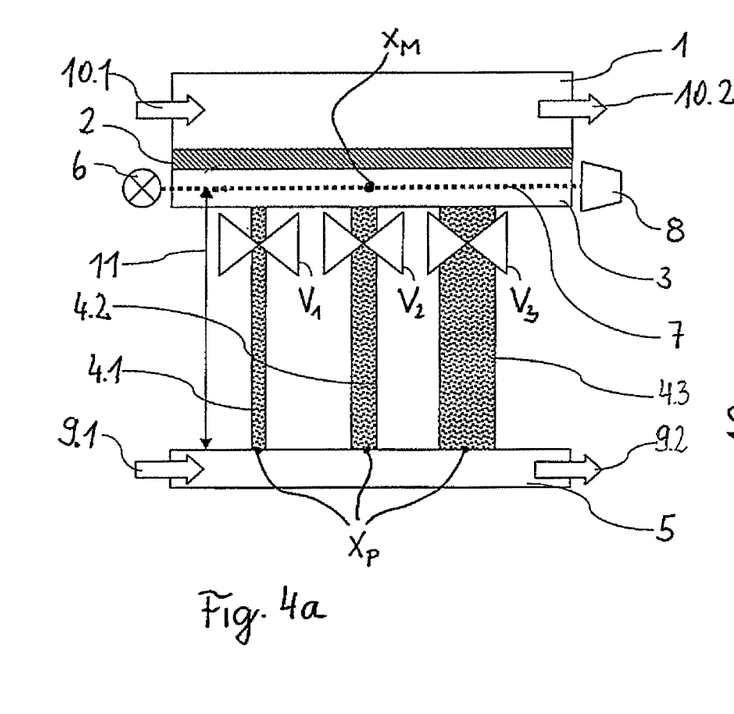
Figure 4B:
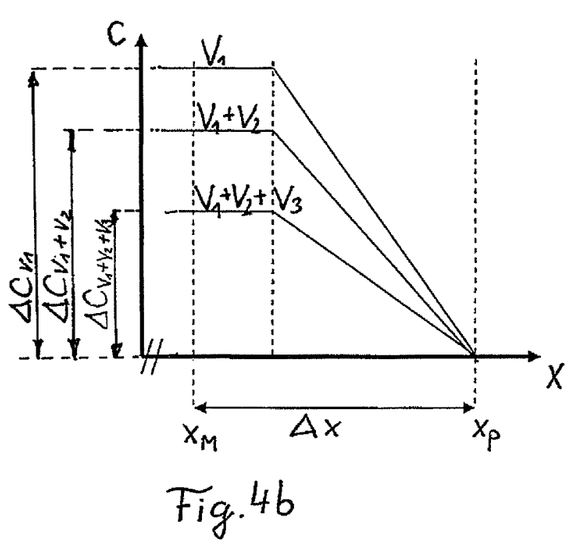

For the purposes of an accelerated setting of the equilibrium state of the permeate mass flux and for increasing the dynamic range during the measurement, a plurality of hollow conducting elements 4.1, 4.2, 4.3, with mutually different internal clear cross-sectional areas $A_G$, are arranged in parallel, as illustrated in FIG. 4a. Valves V1, V2, V3 can be used to open and/or seal the hollow conducting elements 4.1, 4.2, 4.3, and so the clear internal cross-sectional area $A_G$, through which the permeate can diffuse, can be influenced. In the case where the permeation of the barrier element 2 to be determined is very low (concentration lies below the detection limit of the sensor/detector) or if the permeate concentration in the region of the measurement is too low, an increase in the measurement sensitivity is achieved by reducing the clear internal cross-sectional area $A_G$. To this end, the hollow conducting elements 4.3, 4.2 are successively sealed at the respective valves, starting with the largest clear cross-sectional area $A_G$. As can be gathered from the schematic graph of the concentration gradient of the permeate in FIG. 4b, this leads to an increase of the permeate concentration at the position $x_M$.

However, in a non-illustrated form, there is also the option of respectively carrying out one measurement for each hollow conducting element 4.1, 4.2, 4.3 along the diffusion path 11, using a single-position and/or two-position measurement.

Figure 5A:
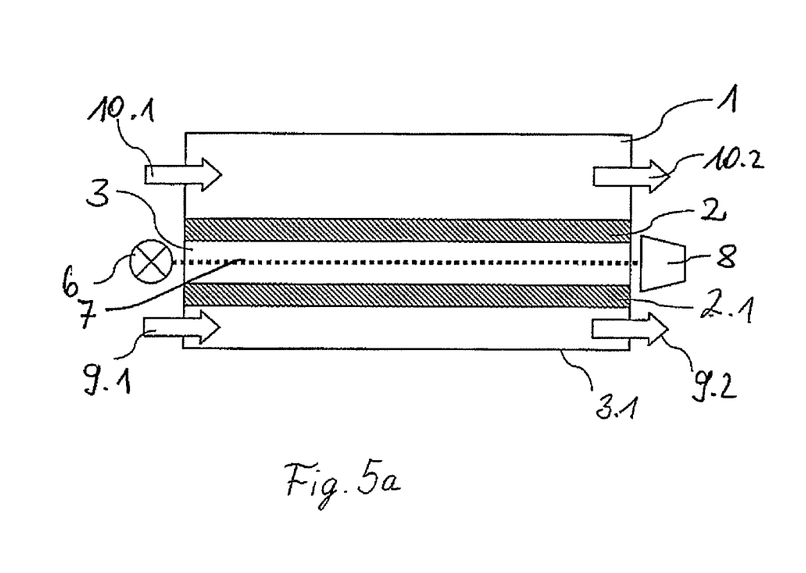
Figure 5B:
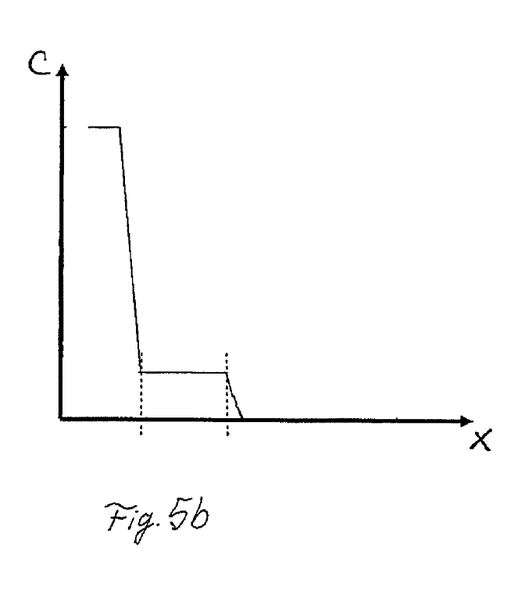

In the embodiment illustrated in FIG. 5a of a device for determining the permeation rate of a barrier element or ultrabarrier element, a second barrier element 2.1 with a known permeability and a second measurement chamber 3.1 are arranged following a first measurement chamber 3.

The invention claimed is:

1. Device for determining the permeation rate of a barrier element, in which
    a barrier element (2), at least in sections, forms a separation with a permeable cross-sectional area $A_B$ between a test gas space (1) and a measurement chamber (3), the test gas space (1) containing a gas, to be permeated, at constant partial pressure,
    characterized in that
    at least one hollow conducting element (4) with a permeate sink (5) is arranged or formed on the measurement chamber (3) in such a way that a flow-free diffusion path (11), through which a permeate can diffuse, is formed starting from the barrier element (2), through the hollow conducting element (4), up to the permeate sink (5), wherein
    the hollow conducting element (4) has a cross-sectional area $A_G$, modified compared to the cross-sectional area $A_B$ at at least one position,
    with the permeate concentration being measurable in a non-invasive fashion using at least one detector (8,8.1, 8.2) at at least one known position along the measurement chamber (3) or the hollow conducting element (4).

2. Device according to claim 1, characterized in that, at at least one known position $X_i$, radiation emitted by at least one radiation source (6, 6.1, 6.2) having at least one wavelength, which corresponds to an absorption wavelength of a permeate, is directed at at least one detector (8, 8.1,8.2), guided through or perpendicular through a volume section d of the diffusion path (11).

3. Device according to claim 1, characterized in that in order to measure the permeate concentration in the measurement chamber or in the hollow conducting element (4), use is made of FTIR spectroscopy, cavity-ring-down spectroscopy, photoacoustic spectroscopy, optical spectroscopic techniques, or laser-diode spectroscopy.

4. Device according to claim 1, characterized in that a hollow conducting element (4) is longer than the distance between the barrier element (2) and the permeate sink (5).

5. Device according to claim 1, characterized in that a gas atmosphere having air, $O_2$, He, Ar, $H_2$ or preferably $N_2$ is formed within the measurement chamber (3), the hollow conducting element (4) and the permeate sink (5).

6. Device according to claim 1, characterized in that at least two hollow conducting elements (4) with different internal cross-sectional areas $A_G$ are arranged in parallel between the measurement chamber (3) and the permeate sink (5), wherein the cross-sectional areas $A_G$ of the at least two hollow conducting elements (4) differ from the cross-sectional area $A_B$.

7. Device according to claim 1, characterized in that adsorbers and/or absorbers for permeate is/are present in the permeate sink (5) and/or dry purge gas flows there for removing the permeate.

8. Device according to claim 1, characterized in that a second barrier element (2.1) with a known permeability is arranged following the measurement chamber (3) and a second measurement chamber (3.1) is arranged following the second barrier element (2.1).

9. Device according to claim 1, characterized in that at least one window element for the entry and/or exit of laser radiation is/are present on a measurement chamber (3, 3.1) or a hollow conducting element (4).

10. Device according to claim 1, characterized in that the length of the diffusion path, the length of the diffusion path section $\Delta x$, the size of the clear cross-sectional area $A_G$ and/or the length of the volume element d of the diffusion path, through which the radiation radiates, can be set for setting the respective measurement sensitivity.

11. Method for determining the permeation rate of a barrier element, in which
    gas at least to be permeated is continuously supplied to and/or kept at constant partial pressure in a test gas space (1), wherein a
    permeate, which permeated through a cross-sectional area $A_B$ of a barrier element (2), diffuses without flowing through a measurement chamber (3) along a diffusion path (11) through at least one hollow conducting element (4), with at least one clear cross-sectional area $A_G$ different from the cross-sectional area $A_B$, into a permeate sink (5) and is adsorbed and/or absorbed and/or removed from there such that a constant permeate concentration below the detection limit of a t lea one detector (8, 8.1, 8.2) is set at the permeate sink (5), with, in the process, radiation having at least one absorption wavelength of a respective permeate, which is emitted by at least one radiation source (6, 6.1, 6.2) being directed through the measurement chamber (3) or through at least one hollow conducting element (4), guided through one volume element d of the diffusion path (11) at at least one known position $x_i$, in the case of a single-position measurement and through respectively one volume element $d_i$, $d_{ii}$ of the diffusion path (11) at at least two known positions $x_i$, $x_{ii}$ in the case of a multiple position measurement, directed at said at least one detector (8,8, , 8.2), and, in the process, the intensity modification of the radiation as a result of the permeate concentration being detected and the permeate concentration $c_i$, $ci_i$ being determined therefrom, wherein the change in the permeate concentration $\Delta c$ being determined along a diffusion path section $\Delta x$, which corresponds to the distance between the known position $x_i$, and the permeate sink (5) or the distance between at least two known positions $x_i$, and $x_{ii}$ along the diffusion path (11)

and the permeation rate $PR_B$ of the barrier element (2) is calculated from the concentration gradient of the permeate $\Delta c/\Delta x$, formed from $\Delta c$ and the length of the diffusion path section $\Delta x$, multiplied by the quotient of the clear cross-sectional area $A_G$ of the diffusion section $\Delta x$ and the permeable cross-sectional area $A_B$ of the barrier element (2) $A_G A_B$ multiplied by the negative value of the diffusion constant D of the permeate.

12. Method according to claim 11, characterized in that the measurement chamber (3) and/or the hollow conducting element (4) is/are preconditioned with UV radiation, thermal desorption or by purging of reactive gases.

13. Method according to claim 11, characterized in that radiation is guided perpendicular to or along through a volume element d of the diffusion path (11).

14. Method according to claim 11, characterized in that the permeate concentration is determined at a constant and/or known temperature.

* * * * *